(12) United States Patent
Schwalbe et al.

(10) Patent No.: US 7,413,714 B1
(45) Date of Patent: Aug. 19, 2008

(54) SEQUENTIAL REACTION SYSTEM

(75) Inventors: Thomas Schwalbe, Bad Vilbel (DE);
Klaus Golbig, Maintal-Doernigheim (DE); Michael Hohmann, Darmstadt (DE); Andreas Oberbeck, Wiesbaden (DE); Shahriyar Taghavi-Moghadam, Neu-Isenburg (DE)

(73) Assignee: YMC Co. Ltd., Kyoto (JP)

( * ) Notice: Subject to any disclaimer, the term of this patent is extended or adjusted under 35 U.S.C. 154(b) by 870 days.

(21) Appl. No.: 09/617,068

(22) Filed: Jul. 16, 2000

(51) Int. Cl.
*B01J 19/24* (2006.01)
(52) U.S. Cl. .................. 422/130; 422/62; 422/109; 436/50; 436/55; 700/266; 700/274
(58) Field of Classification Search ............... 422/130, 422/62, 109; 436/50, 55; 700/266, 274
See application file for complete search history.

(56) References Cited

U.S. PATENT DOCUMENTS

| | | | |
|---|---|---|---|
| 3,881,701 A | 5/1975 | Schoenman et al. ........... 259/4 |
| 4,222,671 A | 9/1980 | Gilmore ...................... 366/337 |
| 4,702,073 A | 10/1987 | Melconian ...................... 60/39 |
| 4,728,502 A | 3/1988 | Hamill ........................ 422/116 |
| 4,748,002 A | 5/1988 | Neimark et al. ............. 422/116 |
| 4,894,146 A | 1/1990 | Giddings .................... 209/12.2 |
| 5,122,345 A | 6/1992 | Tabor et al. ................. 422/116 |
| 5,209,906 A | 5/1993 | Watkins et al. .............. 422/200 |
| 5,250,263 A | 10/1993 | Manz ........................... 422/81 |
| 5,273,715 A | 12/1993 | Bridgham et al. ............. 422/63 |
| 5,288,468 A | 2/1994 | Church et al. ................ 422/116 |
| 5,324,483 A | 6/1994 | Cody et al. .................. 422/131 |
| 5,399,317 A | 3/1995 | Stolowitz ..................... 422/99 |
| 5,405,585 A * | 4/1995 | Coassin ....................... 422/100 |
| 5,463,564 A | 10/1995 | Agrafiotis et al. ........... 364/496 |
| 5,468,643 A | 11/1995 | Su et al. ....................... 436/161 |
| 5,482,862 A | 1/1996 | LaPack et al. ................. 436/52 |
| 5,499,650 A | 3/1996 | McArthur et al. ............. 137/625 |
| 5,516,423 A | 5/1996 | Conoby et al. ................ 210/85 |
| 5,534,328 A | 7/1996 | Ashmead et al. ............. 428/166 |
| 5,580,523 A | 12/1996 | Bard ........................... 422/50 |
| 5,595,712 A | 1/1997 | Harbster et al. ............. 422/129 |
| 5,641,400 A | 6/1997 | Kaltenbach et al. ......... 210/198 |
| 5,644,395 A | 7/1997 | Folta .......................... 356/246 |
| 5,658,537 A | 8/1997 | Dugan ........................ 422/191 |
| 5,681,534 A | 10/1997 | Neves ......................... 422/131 |
| 5,690,763 A | 11/1997 | Ashmead et al. ............. 156/60 |
| 5,698,485 A | 12/1997 | Bruck et al. ................. 501/87 |
| 5,705,018 A | 1/1998 | Hartley ....................... 156/345 |
| 5,727,618 A | 3/1998 | Mundinger et al. ......... 165/80.4 |
| 5,730,947 A | 3/1998 | Chaussonnet ............... 422/177 |
| 5,741,466 A | 4/1998 | Bodnaras .................... 422/228 |
| 5,803,600 A | 9/1998 | Schubert et al. ............. 366/144 |
| 5,811,062 A | 9/1998 | Wegeng et al. .............. 422/129 |
| 5,928,880 A | 7/1999 | Wilding et al. ............. 435/7.21 |
| 5,939,024 A | 8/1999 | Robertson ................... 422/101 |
| 5,961,932 A | 10/1999 | Ghosh et al. ................ 422/193 |
| 5,976,472 A | 11/1999 | Chatterjee et al. ........... 422/130 |
| 5,993,750 A | 11/1999 | Ghosh et al. ................ 422/191 |
| 6,036,355 A | 3/2000 | Yant et al. .................... 366/171 |
| 6,036,927 A | 3/2000 | Chatterjee et al. ........... 422/211 |
| 6,063,019 A | 5/2000 | Wade .......................... 494/14 |
| 6,126,723 A | 10/2000 | Drost et al. ..................... 96/4 |
| 6,149,882 A | 11/2000 | Guan et al. ................. 422/211 |
| 6,171,865 B1 | 1/2001 | Weigl et al. ................... 436/52 |
| 6,180,081 B1 | 1/2001 | Poschmann et al. ......... 423/648 |
| 6,190,034 B1 | 2/2001 | Nielsen et al. .............. 366/336 |
| 6,192,596 B1 | 2/2001 | Bennett et al. ................. 34/76 |
| 6,221,226 B1 | 4/2001 | Kopf-Sill .................... 204/602 |

(Continued)

FOREIGN PATENT DOCUMENTS

DE 960 183 3/1957

(Continued)

OTHER PUBLICATIONS

Van den Berg, A et al. 1996. "Modular Concept for Miniature Chemical Systems." *DECHEMA Monographs*: 132:109-23.

*Primary Examiner*—Jill Warden
*Assistant Examiner*—Natalia Levkovich
(74) *Attorney, Agent, or Firm*—Ronald M. Anderson (57) ABSTRACT

An automated sequential reaction system that can be used to either sequentially produce a plurality of different products each requiring a single reaction, or to produce a desired product that requires a series of sequential reactions. A system controller controls an automated reactant supply, a solvent supply, a reaction module, a detector, and a product collector. Prior to initiating any reaction, the system is flushed with solvent and a heat exchanger supplies the reaction module with a temperature-conditioned fluid to maintain the reaction module at a desired temperature. For single reactions, a plurality of reactants are injected into a chemical reactor included in the reaction module. As fluid exits the chemical reactor, the detector determines if the fluid is a desired chemical product or solvent, and routes the fluid to the appropriate receptacle. Once a predetermined volume of a desired product is obtained, the system is flushed with solvent, and a different set of reactants are injected into the chemical reactor to produce the next desired product. The process is repeated until a substance library of the desired products is obtained. For products requiring sequential reaction steps, either a plurality of reactors are employed, or an intermediate product produced by a previous reaction is reintroduced into the reaction module with an appropriate reactant to complete the next sequential reaction.

21 Claims, 4 Drawing Sheets

U.S. PATENT DOCUMENTS

| | | | |
|---|---|---|---|
| 6,264,900 B1 | 7/2001 | Schubert et al. | 422/224 |
| 6,494,614 B1 | 12/2002 | Bennett et al. | 336/36 |
| 6,537,506 B1 | 3/2003 | Schwable et al. | 422/130 |
| 6,656,423 B1 * | 12/2003 | Joslyn | 422/1 |
| 6,701,774 B2 | 3/2004 | Srinivasan et al. | 73/23.42 |
| 6,827,095 B2 | 12/2004 | O'Connor et al. | 137/15.01 |
| 2002/0042140 A1 | 4/2002 | Hagemeyer et al. | 436/34 |
| 2002/0045265 A1 | 4/2002 | Bergh et al. | 436/37 |
| 2002/0080563 A1 | 6/2002 | Pence et al. | 361/677 |
| 2002/0151080 A1 | 10/2002 | Dasgupta | 422/55 |
| 2002/0170976 A1 | 11/2002 | Bergh et al. | 236/49.1 |

FOREIGN PATENT DOCUMENTS

| | | | |
|---|---|---|---|
| EP | 0796654 | | 3/1997 |
| WO | WO87/00139 | | 4/1987 |
| WO | WO93/00625 | | 1/1993 |
| WO | WO9300625 | * | 1/1993 |
| WO | WO 98/38487 | | 3/1998 |
| WO | WO 99/04892 | | 7/1998 |
| WO | WO 98/55812 | | 12/1998 |
| WO | WO99/20395 | | 4/1999 |
| WO | WO 00/34728 | | 6/2000 |
| WO | WO 00/51720 | | 9/2000 |
| WO | WO 00/62914 | | 10/2000 |
| WO | WO 00/62919 | | 10/2000 |
| WO | WO 01/41916 | | 6/2001 |
| WO | WO 01/66245 | | 9/2001 |
| WO | WO 01/68257 | | 9/2001 |
| WO | WO 01/93998 | | 12/2001 |

* cited by examiner

SEQUENTIAL REACTION SYSTEM

FIELD OF THE INVENTION

This invention generally relates to a chemical processing apparatus, and more specifically, to a system for automatically controlling a plurality of sequential chemical reactions.

BACKGROUND OF THE INVENTION

Apparatus for controlling and optimizing the production of chemical substances are well known in the prior art. Factors affecting the design of chemical production equipment and of controlling the equipment include the chemical properties of the desired product and the reactants used, the temperature and pressure required, and the required product volume or production rate. Chemical processing equipment can be specifically designed for a particular reaction, or can be designed to be more generally applicable to a variety of chemical reactions.

For example, the chemical processing equipment employed in large scale production facilities is often optimized for high volume production of a single desired product. In contrast, research laboratories typically use chemical processing equipment designed to produce relatively small volumes of many different products.

Chemical reactors that can be used for more than a single chemical reaction are most suited in processes that require several different sequential reactions. For example, in research settings, small volumes of a number of different yet closely related chemicals may be required, requiring that a series of related yet different chemical manipulations be executed. For such an application, a single reactor can be used to sequentially produce a plurality of different products, by continually providing the reactor with different mixtures of reagents. When the research is directed toward determining optimum parameters for producing a single product, different small batches of the same product are often sequentially produced, under varying process conditions, so that the optimal reaction parameters can be determined.

One of the highest costs of research is associated with skilled labor. Accordingly, it is preferable to automate chemical processing systems used in a research environment to the extent practical. Indeed, it would be desirable to employ a fully automated chemical processing system that is capable of operating continually with minimal operator supervision to generate the desired products. Such a system should preferably include a reactant supply system capable of providing a variety of different selected reactants upon command, so that a plurality of different products can be sequentially produced without operator supervision. Such a system would likely require a product collector capable of separately storing the different desired products that are produced.

U.S. Pat. No. 5,324,483 (Cody et al.) describes a device that includes a plurality of chemical reactors operating in parallel and having the ability to simultaneously synthesize many different compounds. However, given the available space and funding constraints under which many research facilities operate, it would be preferable to employ an automated system with a single reactor that operates continually, with minimal operator attention over a period of time, to provide different selected desired products.

To produce some types of desired products, reactants must undergo a sequence of reactions. Again, in a research laboratory, it would be preferable to carry out such reactions using a single chemical processing system. For example, in the field of biotechnology, many sequential reactions are often required to produce a desired product. Peptides, which are sequences of amino acids, are extremely useful research chemicals that are produced by successively adding selected different amino acids, in the proper order, to a base amino acid or peptide. U.S. Pat. No. 4,748,002 (Neimark) describes a semi-automated chemical processing system optimized to produce different peptides. The system includes a plurality of different reaction chambers operating independently of each other. A reaction chamber is charged with a base amino acid, and the desired peptide is produced by adding additional amino acids with the base amino acid, one by one. Between reactions, the current intermediate product is stabilized and rinsed before a new reaction is initiated by adding the next amino acid. The desired product is not removed from the system until the last amino acid in the sequence has been added, and the entire process may require up to 10 days. While the system disclosed by Neimark enables sequential reactions to be achieved, by its design, the system is optimized and essentially dedicated to the task of synthesizing peptides, and is not useful for most other chemical processing needs.

Recently, much attention has been directed to the use of micro-scale reactors both for the development and production of chemical products, particularly in research applications. Chemical processing systems that employ microreactors offer several clear advantages over more conventional macro-scale chemical processing systems related to cost and efficiency. Accordingly, it would be desirable to provide a sequential chemical processing system that employs a microreactor. The prior art does not teach or suggest such an automated, sequential microreactor-based chemical processing system. By operating continuously, such a system can readily be employed in accumulating substance libraries that will be useful in many different research applications.

SUMMARY OF THE INVENTION

In accord with the present invention, an automated sequential reaction system for sequentially producing a substance library of desired chemical products from a plurality of reactants is defined. Such an automated sequential reaction system includes a system controller adapted to monitor and control the production of the plurality of desired chemical products by the sequential reaction system, and a first automated reactant supply than includes a plurality of separate reactant chambers, each reactant chamber being adapted to be filled with a reactant. The automated reactant supply is controllably connected to the system controller, such that each reactant chamber can be selectively placed in fluid communication with a reaction module to provide a first reactant. In one embodiment, a supply valve is actuated by the system controller to select the first reactant. The reaction module is also controllably connected to the system controller, enabling the automatic production of successive desired chemical products from the reactants supplied by the automated reactant supply. The reaction module includes a general purpose reactor operable to produce a plurality of different desired chemical products from automatically selected reactants. The automated product collector includes a plurality of different product chambers, each adapted to be filled with a different desired chemical product, and the automated product collector is controllably connected to the system controller, which selectively directs the desired chemical products being discharged from the chemical reactor to a selected product chamber.

In one embodiment, the automated reactant supply includes a solvent chamber in addition to the plurality of reactant chambers. The solvent chamber is selectively placed in fluid communication with the reaction module so that solvent contained in the solvent chamber can be used to flush the reaction module. Similarly, the automated product collector preferably further comprises a spent solvent chamber; the spent solvent chamber is adapted to be filled with a spent solvent that has been used to flush the reaction module, under the control of the system controller.

Alternatively, a separate solvent supply and spent solvent reservoir can be included in the automated sequential reaction system. In this alternative embodiment, the solvent supply is selectively placed in fluid communication with the reaction module by the system controller, enabling a flow of solvent through the reaction module. Spent solvent exiting the reaction module is directed by the system controller through an outlet valve controlled by the system controller, and into the spent solvent reservoir, rather than into product chambers.

Preferably, the automated sequential reaction system also includes a detector in fluid communication with an outlet of the reactor, and controllably connected to the system controller. The detector produces a signal indicative of the type of material being discharged from the reactor outlet, so that a desired chemical product is directed to the automated product collector, and the spent solvent is directed into the spent solvent reservoir. If no detector is included, the system controller can direct the material exiting the chemical reactor into the automated product collector or the spent solvent reservoir based on the known flow rates of the reactants and solvent through the reaction module.

The automated sequential reaction system preferably also includes a heat exchanger, controllably connected to the system controller and in fluid communication with the reaction module, which provides a temperature-conditioned fluid that is circulated through the reaction module so that the system controller can control a temperature within the chemical reactor. A pump included in the automated sequential reaction system is controlled by the system controller to achieve a flow rate of the reactants or solvent through the reaction module. The pump has an inlet in fluid communication with the automated reactant supply (or supply valve) and an outlet in fluid communication with an inlet to the reactor.

In one embodiment, the chemical reactor is a microreactor. The automated sequential reaction system may include a residence time chamber in fluid communication with an outlet of the reactor and with an inlet of the detector to provide additional time for the desired chemical product to be produced. A second automated reactant supply is included in one preferred embodiment, the second automated reactant supply being controllably connected to the system controller so that each separate reactant chamber in the additional automated reactant supply can be selectively coupled in fluid communication with the reaction module to supply a second reactant to the reaction module to form the desired chemical products.

Preferably the system controller includes a memory, a processor, and a user interface. The memory stores machine instructions that are executed by the processor to effect automatic control of the automated sequential reaction system. In one embodiment, the system controller is a personal computer.

Another aspect of the present invention is directed to a method for producing a substance library of chemical compounds. The method employs a chemical processing system that includes a reactant supply containing a plurality of reactants, and a chemical reactor. The steps of the method are generally consistent with the functions of the elements in the apparatus discussed above.

The present invention can also be used to sequentially generate a substance library whose products require a production process that includes a series of sequential reactions. The system controller automatically controls the production process, by selecting reactants from a plurality of automated reactant supplies, for input to a plurality of chemical reactors, and controls a solvent supply to flush each chemical reactor before reactants are introduced to produce any desired chemical product. After flushing with the solvent, at least one reactant is injected into a first chemical reactor, causing a chemical transformation that produces an intermediate product. The intermediate product is then automatically injected into a successive chemical reactor, along with another reactant (if required), and this process is repeated until a desired chemical product is formed. A single reactor can be used if the intermediate is injected back into the same chemical reactor for additional processing, after the chemical reactor is flushed with solvent.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Exemplary Application of the Present Invention

The automated sequential reactor system of the present invention can be continually operated to produce substance libraries, which are expected to be of great benefit in many phases of research. For instance, it is often useful to study how a particular chemical compound reacts with a group of related, yet different chemical compounds. As a specific example, consider an experimental compound "X" that is being studied as a potential raw material for producing a drug. In this example, it is assumed that "X" must be combined with a chemical compound that is a base (i.e., a compound having a pH over 7.0) in order to produce the drug. It would be desirable to react chemical "X" with a substantial number of different bases, to determine the yield from the reaction with each base. From the results of such tests, the relative costs of each base can be compared, to determine the base that produces the highest yield, at the lowest cost.

Of course, there are many other research situations in which reacting one chemical with a wide variety of different chemicals is desirable. In the above example, a sequential reaction system in accord with the present invention is employed to generate a substance library, by sequentially reacting "X" with a variety of different bases. In fact, such a sequential reaction system can be first employed to sequentially generate a substance library of different bases, and then employed to sequentially combine those bases with "X", to generate a second library of the reaction products of "X" and each base in the substance library of different bases. However, the automated system of the present invention can be used to create a wide variety of substance libraries for many different purposes and is clearly not limited to the specific example discussed above.

An important aspect of the present invention is its automated operation. An operator is only required to provide the system with appropriate reactants, and the system will be automatically controlled in accord with the steps defined in a software program to generate the desired chemical product(s). Preferably, the system will operate continuously, ensuring that system resources will be utilized even when an operator is not present.

DETAILS OF THE PRESENT INVENTION

Figure 1:
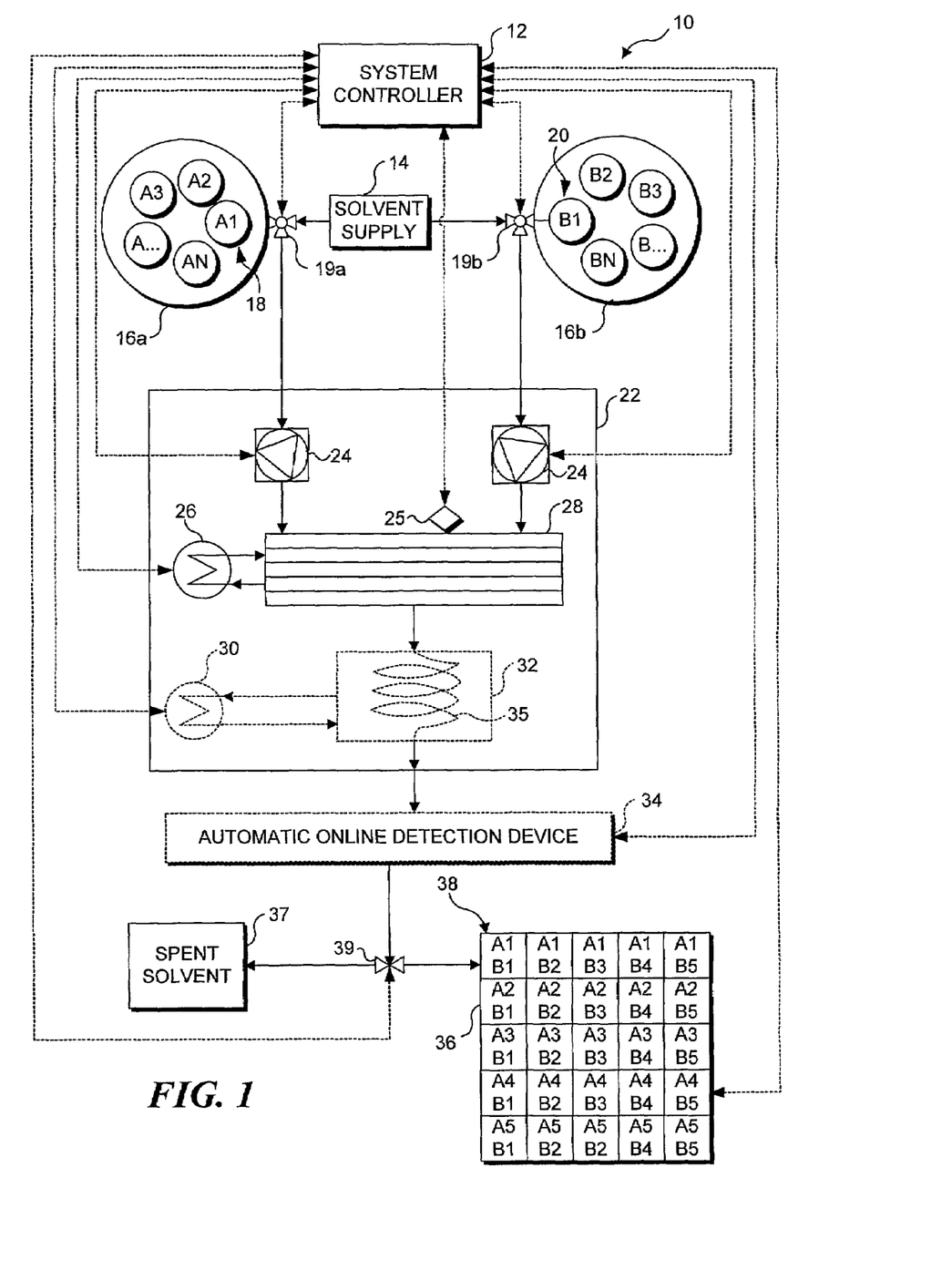
FIG. 1 is a block diagram of the functional elements of a sequential reaction system in accord with the present invention.

FIG. 1 illustrates the functional elements of an automatically controlled sequential reaction system 10. A system controller 12 is used to control the system, including selecting reactants and controlling reactant flow rates, solvent flow rates, temperature conditions, pressure conditions, and residence times. System controller 12 is operatively connected to a supply valve 19a, which is associated with selecting reagents from an automated reactant supply 16a, a supply valve 19b, which is associated with selecting reagents from an automated reactant supply 16b, a reaction module 22, an optional automatic online detection device 34, and an outlet valve 39, which controls the fluid flow into an automated product collector 38, which includes a plurality of separate fluid collection chambers 36. Supply valves 19a and 19b and outlet valve 39 include a prime mover (not shown), which may comprise a stepping motor or solenoid, that is controlled by system controller 12 to select the input port for the supply valve, and the output port for the outlet valve. Optionally, supply valve 19a may be integral with automated reactant supply 16a, and supply valve 19b may be integral with automated reactant supply 16b. Similarly, outlet valve 39 may be integral with automated product collector 38. Reaction module 22 includes two pumps 24, one of which has an input coupled to the output of supply valve 19a and the other of which has an input coupled to the output of supply valve 19b, the output of both supply valves being coupled to a chemical reactor 28. A heat exchanger 26, a temperature sensor 25, and an optional residence time chamber 32 with its own optional heat exchanger 30 are also included within the reaction module. Heat exchanger 26 is coupled in fluid communication with chemical reactor 28 and provides a temperature conditioned fluid to control the temperature within the chemical reactor. Similarly, if used, optional heat exchanger 30 is coupled in fluid communication with residence time chamber 32 and provides a temperature conditioned fluid for controlling the temperature within the residence time chamber. Alternatively, the temperature conditioned fluid from heat exchanger 26 can also be coupled in fluid communication with residence time chamber 32, to control its temperature with the temperature-conditioned fluid circulated therethrough. System controller 12 is controllably connected to pumps 24, a temperature sensor 25 that is disposed on or in the chemical reactor (to receive a temperature indicative signal that it produces), heat exchanger 26, and optional heat exchanger 30.

Automated reactant supply 16a includes a plurality of different reactants 18. As illustrated, the plurality of reactants 18 within automated reactant supply 16a include reactants A1-AN. It should be understood that automated reactant supply 16a can beneficially incorporate a wide variety of different reactants, limited in number only by the physical limitations of the device. Thus, the illustration of reactants A1-AN should be considered exemplary, and not limiting on the scope of the present invention. Similarly, automated reactant supply 16b contains a plurality of reactants 20, which include reactants B1-BN, also shown in an exemplary fashion.

The volume of each individual reactant (A1-AN) included within automated reactant supply 16a is a function of a volume of a desired product. It is anticipated that sequential reaction system 10 will be beneficially employed in research laboratories, where the relative volumes of reactants used for research activities are relatively small. Under such circumstances, the volume of individual reactants provided will likely be on the order of tens to hundreds of milliliters. However, such volumes can readily be significantly scaled up for production volumes, and thus, are only exemplary of a preferred embodiment intended for research, and not limiting on the scope of the invention. While it is anticipated that the volumes of reactants A1-AN will often be equal, it should be understood that different volumes of individual reactants can also be provided as desired, since the volume of reactant introduced into the chemical reactor is automatically controlled. Similarly, with respect to automated reactant supply 16b, the volumes of individual reactants B1-BN are again a function of a volume of a desired product. Preferably, sufficient reactants will be included in automated reactant supply 16b to fully react with the reactants provided by automated reactant supply 16a to produce the required volumes of the specific desired chemical products to be prepared by the system.

It should be understood that the number of different reactants required varies with the type of sequential reaction being implemented to produce the desired chemical products comprising a specific substance library. Many chemical reactions can be achieved using two reactants, hence two automated reactant supplies are shown. However, some reactions require additional reactants, and if sequential reaction system 10 is to be used to facilitate such reactions, additional automated reactant supplies can readily be added as needed. Furthermore, some reactions require only a single reactant to generate a desired chemical product (such as reactions involving passing a reactant through a catalytic reactor that transforms the reactant into a different chemical substance), and it is anticipated that in some applications of the present invention, only a single automated reactant supply would be included into the automated sequential reaction system, which might then be used to produce a product library from reactions involving only a single reactant at a time, but different reactants for each of the desired chemical compounds comprising the product library.

As illustrated, automated reactant supplies 16a or 16b each include 1-N reactant chambers. If each reactant chamber in automated reactant supplies 16a and 16b contains a different reactant, then $N^2$ different chemical products could be produced by combining one reactant from automated reactant supply 16a with one reactant from automated reactant supply 16b. The relative volumes of each reactant chamber are not required to be identical, although such a configuration will likely be easier to manufacture and use. In some instances, it will be useful to include the same reactant in more than one reactant chamber. For instance, if a given automated reactant supply 16a contains five reactant chambers of 10 ml each, and a particular series of reactions required to produce a desired product library will consume 40 ml of reactant X, then that 40 ml can be distributed into four separate reactant chambers. Generally, the reactants will be liquids, though gases may also be used. Solid reactants will generally be dissolved or suspended in a liquid for ease of handling and processing in the system.

The particular designs of automated reactant supplies 16a and 16b are not critical. It is contemplated that a rotary design that effectively integrates the supply valve will rotate the assembly to bring a selected reactant chamber into alignment with an output port to provide the reactant within that selected reactant chamber to the reaction module. Such a device will be rotated in response to a command from system controller 12. However, a plurality of standard chemical product containers and/or laboratory glassware, properly connected together to the supply valve will alternatively enable the selection of a specific reactant in response to a command from system controller 12 being received by the supply valve, to enable the specific reactant that is thus selected to be provided as an input to the chemical reactor. Automated product collector 38 illustrates another type of automated selection system, commonly referred to as a matrix board, in which a plurality of containers (such as test tubes) are arranged in a matrix. Such a system can also be employed for either or both of automated reactant supplies 16a and 16b, using one of the supply valves to select a reactant for input to the chemical reactor.

Supply valves 19a and 19b are also used to selectively couple solvent from a solvent supply 14 in fluid communication with the reaction module. Because a plurality of different reactants are employed in sequential reaction system 10, solvent supply 14 is used to flush the system before reactions, and/or before any reactants are injected into reaction module 22, to ensure that no undesired cross reactions occur due to reactant or product residue that may remain in the system. Before initiating any reaction, system controller 12 will selectively enable a flow of solvent from solvent supply 14 to flush reaction module 22 with solvent. It is anticipated that instead of using a separate solvent supply 14, solvent can alternatively be stored in one (or more) reactant chambers (A1-AN, B1-BN) within automated reactant supply 16a or 16b. However, this approach will reduce the number of different reactants available to sequential reaction system 10. Such an embodiment is likely to be useful when the volume of solvent required is minimal. In general, it is expected that a solvent such as diethylether can be beneficially employed to flush the system between reactions, during the production of the substance library. However, there may be occasions where a specific product is either incompatible with diethylether, or which requires a different specific solvent. In such cases, either an additional solvent supply can be provided, solvent supply 14 can be separated into a plurality of different solvent chambers, or the less frequently used solvent can be stored within one of or both of automated reactant supplies 16a and 16b.

Supply valves 19a and 19b are illustrated disposed immediately adjacent to automated reactant supplies 16a and 16b to minimize the volume of the fluid lines that extend between the supply valves and the corresponding automated reactant supplies, since these fluid lines will not be flushed with solvent that flows from solvent supply 14 to the supply valves and into the reaction module. Preferably, the individual reactant chamber of automated reactant supply 16a or 16b that is selected to be in fluid communication with reaction module 22, is placed in fluid communication with the respective supply valve 19a or 19b without any appreciable fluid line (i.e., the outlet of the reactant chamber is connected directly to the input of the supply valve) to eliminate any appreciable volume in a common fluid line that is not flushed with solvent, thereby preventing cross contamination from occurring when reactants are changed.

Because the flow rate of the system is a programmed parameter, system controller 12 enables the proper volume of reactants and solvent to be provided by controlling the time duration for which supply valves 19a and 19b are in fluid communication with their respective automated solvent supplies or with solvent supply 14. To enhance the accuracy of the volumes delivered, flow sensors can be added to provide system controller with a feedback signal indicative of real time flow rates, to verify that the desired programmed flow rates have been achieved. If the programmed flow rates have not been achieved, system controller 12 can manipulate the flow rates (i.e., the supply valves) to ensure that the desired volumes of solvent and reactants are provided.

As discussed above, selected reactant chambers in automated reactant supply 16a and 16b are coupled in fluid communication with the input to reaction module 22 via their respective supply valves 19a and 19b. In particular, FIG. 1 indicates that specific reactants A1 and B1 are selected by supply valves 19 for input to reaction module 22. The purpose of reaction module 22 is to react one or more reactants under controlled conditions, thereby facilitating a chemical reaction or transformation that will create a desired chemical product. While reaction module 22 as illustrated in FIG. 1 includes pumps 24, heat exchanger 26, and a stacked plate reactor 28, and optionally includes residence time chamber 32, and heat exchanger 30, many different types of reaction modules can instead be used in a sequential reaction system in accord with the present invention. Thus, reaction module 22 as described in this preferred embodiment is only exemplary, and should not be considered limiting on the scope of the present invention. Any general reaction module capable of automatically producing a desired chemical product utilizing one or a variety of different reactants can be employed in the present invention.

Because it is anticipated that the present invention will be particularly useful in research environments that do not require large volumes of product to be generated, it is anticipated that a reaction module that incorporates a microreactor will be particularly suitable. Such a microreactor is described in commonly assigned, co-pending U.S. patent application, Ser. No. 09/496,999, entitled "MINIATURIZED REACTION APPARATUS," which was filed Feb. 3, 2000, the disclosure (including the specification and drawings) of which is hereby specifically incorporated herein by reference. Furthermore, a suitable reaction module is described in commonly assigned, co-pending U.S. patent application, Ser. No. 09/578,224, entitled "MODULAR CHEMICAL PRODUCTION SYSTEM INCORPORATING A MICROREACTOR," which was filed on May 24, 2000, the disclosure (including the specification and drawings) of which is hereby specifically incorporated herein by reference.

Pumps 24 are included in reaction module 22 to ensure a controlled flow of reactants from automated reactant supplies 16a and 16b (and solvent, from solvent supply 14) into reactor 28. It should be noted that pumps 24 can be omitted from reaction module 22, if other means for driving selected reactants through chemical reactor 28 are provided. For example, a gravity feed system, in which automated reactant supplies 16a and 16b are disposed at a higher elevation than reaction module 22, can be employed so that the force of gravity will cause the selected reactants to flow through chemical reactor 28. It should be noted that chemical reactor 28, and the particular reaction being facilitated will typically have associated therewith an optimal flow rate, and a gravity feed system may not be capable of providing that optimal flow rate. Another approach to provide the required flow rate is to use a pressure source that forces the reactants through the chemical reactor. Or a vacuum source can be connected to automated product collector 38 to draw reactants from automated reactant supplies 16a and 16b, through reaction module 22, and then draw the desired chemical product that is produced into product collector 38. If the reactants are in a gaseous state, rather than a liquid state, flow rates of the reactants are preferably controllable using the supply valves, if the gases are under pressure when supplied to the chemical reactor. Standard gas bottles or commercial grade gas cylinders, and an associated supply valve system controlled by system controller 12 will then comprise automated reactant supplies 16a and/or 16b. Finally, pumps 24 can alternatively be disposed external to reaction module 22.

If one or more pumps 24 are included, a variety of different types of pumps can be beneficially employed. If the reactants are extremely flammable, it is anticipated that explosion-proof pumps will be used. As illustrated, each automated reactant supply has a separate pump associated with that reactant supply, although it is envisioned that a single pump unit could be used, as long as the reactants are not mixed until they enter chemical reactor 28. It is anticipated that heat exchanger 26 will incorporate its own pump (not separately shown) to supply the temperature-conditioned heat transfer media to the chemical reactor, controlled by system controller 12, so that the flow rates of the heat transfer media into chemical reactor 28 can be controlled. While not shown, it is expected that pressure sensors and filters can optionally be used in association with pumps 24. A signal produced by the pressure sensors will provide confirmation to system controller 12 that the reactants are flowing, and the filters can be employed to filter any particulate matter that may have contaminated automated reactant supply 16a or 16b. In a preferred embodiment, in which the reaction module incorporates a microreactor, these filters are particularly important, since the fluid channels within a microreactor are characteristically very small in size. Thus, even relatively small particulates can clog these channels and significantly impair the efficiency of the microreactor. Preferably system controller 12 is programmed to alert a user to check the filters when pressure sensors indicate a change in pressure in the system, as such a pressure change may be indicative of a clogged filter. During the flushing process, it is anticipated that pumps 24 will be used to increase the flow rate of solvent through the system, to reduce the time required for flushing, thereby increasing the throughput of the system.

With respect to heat exchanger 26, it is preferred that the heat transfer media used be fluidic in nature. While solid phase heat transfer media are known in the art (such as silica), assuring a continual flow of such solid phase heat transfer media through small passages in heat exchangers can be difficult, and in general, fluidic heat transfer media are preferred in the present invention.

It should be noted that FIG. 1 does not attempt to illustrate the fluid paths of reactants within reactor 28. The two reactants (or one reactant) that were selected flow into chemical reactor 28, and a single desired chemical product exits the chemical reactor. The path from the chemical reactor is illustrated as being in fluid communication with optional residence time module 32. If the optional residence time module is not required for the process being carried out by the system, the desired chemical product flows directly to optional detector 34 or if the detector is not included, to product collector 38.

While in one preferred embodiment, the chemical reactor within reaction module 22 is a microreactor, a macro-scale reactor could alternatively be used in conjunction with the present invention. Microreactors are generally characterized as incorporating fluidic structures of less than 1 mm in size, especially with respect to reactant fluid pathways. However, it should be understood that the present invention is not limited to reaction modules that include a microreactor, as the reaction module can incorporate a chemical reactor whose fluidic structures are larger in size than the micro-scale fluidic structures generally associated with microreactors.

Although it is possible to design a chemical reactor to facilitate one specific reaction, it is preferable that the chemical reactors used in sequential reaction system 10 be of a more general design that will support the production of as many different desired chemical products as possible. Those of ordinary skill in the art will readily recognize that chemical reactors capable of mixing two or more reactants together under controlled temperature and other controlled conditions can facilitate the production of a wide variety of different products. As noted above, however, not all reactions require the mixing of reactants, such as reactions involving passing one or more reactants over a catalyst impregnated surface, electrochemical reactions, or photochemical reactions that are initiated by the application of light of the appropriate wavelength. Other process parameters can be beneficially incorporated into reactors for use in the present invention including magnetic, piezoresistive, piezoelectric, shape memory, radioactive, catalytic, optical, electromagnetic, and electrostatic parameters. Any such parameter is preferably capable of being controlled by system controller 12. Regardless of the control parameter used by the chemical reactor, the chemical reactors employed should preferably be able to produce a wide variety of products, rather than being limited to the production of only a narrow range of products, such as peptides or DNA sequences.

Suitable chemical reactors for the present invention should preferably enable the precise temperature control of the reactants and the product, so that yield and product quality can be enhanced. Thus, reaction module 22 preferably includes at least one temperature sensor 25 disposed adjacent to (as shown) or within (not shown) chemical reactor 28. These temperature sensors produce a signal indicative of the temperature being monitored that is electrically connected to system controller 12, and the system controller 12 uses the signals produced by the temperature sensor(s) to adjust the flow rates and other relevant parameters of the heat transfer fluid provided by heat exchanger26 to maintain the desired temperature parameters within reactor 28.

Depending on the particular design of the chemical reactor disposed within the reaction module, and the particular reaction being facilitated, it is often beneficial to include residence time chamber 32. When the residence time chamber is included, it is preferable to maintain the optimal reaction temperature within the residence time chamber, and this temperature will typically equal that maintained in stacked plate chemical reactor 28 (or the alternative type of reactor provided) by heat exchanger 26. As noted above, either optional heat exchanger 30 can be used for this purpose, or heat exchanger 26 can be used to service both optional residence time chamber 32 and stacked plate chemical reactor 28.

In one embodiment residence time chamber 32 includes a helically-coiled capillary passage 35, the length of the capillary passage controlling a residence time of the reactants in the residence time module. In a preferred embodiment in which chemical reactor 28 is a microreactor, capillary passage 35 is of sufficient length to achieve a 45-minute residence time at a flow rate of one milliliter per minute. Generally, a residence time of 45 minutes is sufficient for the majority of most chemical reactions to reach completion. If it is known that a particular chemical reaction can benefit from an increased residence time, an additional residence time chamber can be added downstream of residence time chamber 32, or a longer capillary passage can be used in place of capillary passage 35. It should be noted that while as shown in FIG. 1 that optional residence time chamber 32 is included within reaction module 22, residence time chamber 32 can also be provided as a separate module, rather than in the reaction module. It should also be noted that residence time chambers not incorporating coiled capillary passage 35 can also be beneficially employed to provide additional time for incompletely reacted reactants exiting reactor 28 to completely react to generate the desired product. As long as the residence time chamber (or residence time module) provides a sufficient volume for the incompletely reacted mixture of reactants exiting the reactor to reside in until the reaction is complete, the particular physical configuration of the sufficient volume is not critical.

Various reactions can be performed in the system that are pressure dependent. For example, reactions involving decreasing volumes, increasing boiling points, and increasing gas concentrations in a liquid phase are pressure dependent. Thus, it may be desirable to enable a reaction to occur at a predefined pressure. To increase the pressure along a reaction path requires a throttle at the distal end of the reaction path. At least partially closing such a throttle causes pumps 24 to produce a higher pressure in the reaction module in order to maintain a constant flow rate. Such a pressure control can be achieved by utilizing a proportional valve as outlet valve 39, so that it is controlled by the system controller to selectively vary a pressure within the sequential reaction system. Product valve 39, as described in detail below, is also used to select where the material exiting reaction module 22 is directed (i.e., to automated product collector 38 or to spent solvent reservoir 37).

Spent solvent exiting reaction module 22 can pass through optional automatic online detection device 34. Many different types of analytical instruments can be used as an online detection device. In general, online detection device 34 samples fluid exiting reaction module 22 and determines if the fluid is spent solvent that has been used to flush reaction module 22, or a desired chemical product generated by the combination and reaction of reactants from automated reactant supply 16a and automated reactant supply 16b. Those of ordinary skill in the art will readily understand that given a known supply of reactants, a known type of solvent, and knowledge of the products expected from the combinations of the selected reactants, differentiating between a product and the spent solvent is readily achievable by a number of different detection devices. Regardless of the detection scheme employed, the results are communicated to system controller 12, which then manipulates outlet valve 39 to divert spent solvent to spent solvent reservoir 37, or a desired chemical product to automated product collector 38.

While the particular analytical device used is not critical, it is anticipated that online devices are preferable. The term "online" refers to a detector's ability to continually analyze the product/spent solvent stream in real time. An online detector is preferable because such a detector will generate a continuous output signal that is supplied to system controller 12, thus enabling the system controller to immediately respond to a change in the material exiting the reaction module, minimizing both product loss and dilution of the desired chemical product being collected with spent solvent. A refractive index based spectrophotometer represents one preferred type of online detector, although online devices such as ultraviolet (UV) spectrum detectors, ultraviolet-visible (UV-VIS) spectrum detectors, and diode array detectors can be beneficially employed. Additionally, detectors that are not "online," but which are capable of cycling on and off rapidly, such as FT-IR spectrophotometers, are also expected to be useful as a detector in this application. By rapidly cycling on and off, such detectors can generate nearly continuous output signals. In any event, advantageous characteristics of any detection device will include a relatively low cost, a relatively quick response time, and the ability to differentiate from among a wide variety of organic compounds.

The detection device is considered an optional component, because system controller 12 precisely controls the flow rates of reactants through the system, and given a known system volume, the system controller can determine with precision when changes between a desired chemical product and solvent exiting reaction module 22 occur, and thus, can control outlet valve 39 to divert spent solvent to spent solvent reservoir 37 and the desired chemical product to automated product collector 38. The incorporation of detection device 34 provides a check to ensure that product and spent solvent are properly separated. If the value of the products being produced is high, as is the case with many experimental compounds used in research applications, then it will likely be desirable to include detection device 34 to safeguard the desired chemical product being produced and collected. It should also be noted that incorporating flow sensors within sequential reaction system 10 to verify that the flow rate conditions commanded by system controller 12 have actually been achieved provides system controller 12 with a feedback signal that can be used to confirm that the material exiting reaction module 22 changes between the desired chemical product and the spent solvent. Those of ordinary skill in the art will readily recognize that given flow rate data and known volumes of the fluid paths in the system, the actual volumes delivered can readily be determined.

As shown in FIG. 1, reactants A1 and B1 enter reaction module 22, pass through pumps 24, chemical reactor 28, optional residence time chamber 32, and exit reaction module 22 as the desired chemical product A1B1. Upon reaching online detection unit 34, product A1B1 is recognized as a desired chemical product, rather than a solvent, and system controller 12 actuates outlet valve 39 to ensure that desired chemical product A1B1 is directed into automated product collector 38. After the desired volume of desired chemical product A1B1 has been collected, system controller 12 will actuate supply valves 19a and 19b to select the solvent, which is used to flush reaction module 22. Once online detection device 34 indicates that solvent is exiting reaction module 22, system controller 12 manipulates product valve 39 to ensure that spent solvent is directed into spent solvent reservoir 37. Alternatively, based on known flow rates (possibly confirmed by flow rate sensors as noted above) system controller 12 will determine at what point all of product A1B1 should have exited reaction module 22, so that spent solvent used to flush the system after product A1B1 has been processed can be diverted to spent solvent reservoir 37.

Preferably automated product collector 38 includes sufficient product chambers to accommodate all of the desired chemical products produced by the system. As shown, automated reactant supply 16a and 16b each include five reactant chambers, thus automated product collector 38 should need at most 25 product chambers. As noted above with respect to automated reactant supply 16a and 16b, the particular design of automated product collector 38 is not critical. While the matrix board style automated product collector 38 illustrated in FIG. 1 is expected to be able to accommodate a large number of products in a compact design, it is also contemplated that a rotary design or other configuration that is selected by outlet valve 39 as discussed above can also be beneficially employed to ensure that the desired chemical product is directed into the proper chamber. An automated product collector that comprises a rotary device as the output valve will be rotated in response to a command from system controller 12 until a desired product chamber (A1B1-ANBN) is in fluid communication with the reaction module. Alternately, a plurality of standard chemical product containers and/or laboratory glassware, properly connected with fluid lines to a separate multi-port valve (not separately shown) that will enable the selection of an individual product collection chamber upon receipt by the multi-port valve of a command from system controller 12. If desired, spent solvent can be accumulated in one or more designated fluid chambers within automated product collector 38, if sufficient other chambers are available for collecting the desired chemical products.

Figure 2:
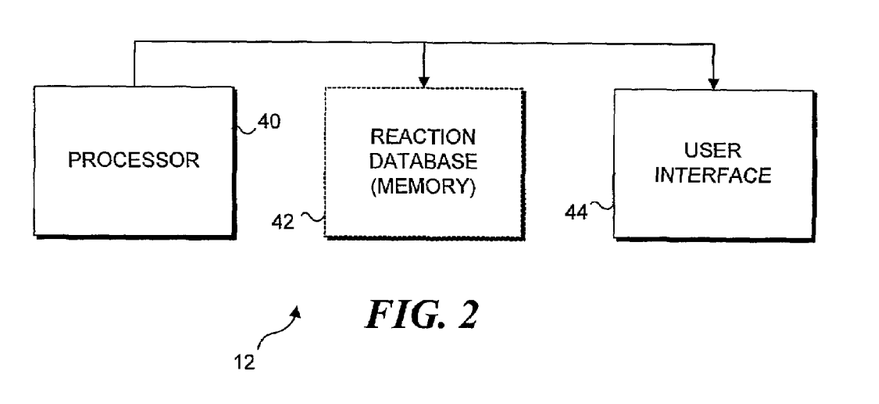
FIG. 2 is a simplified block diagram illustrating the functional elements of a system controller.

As noted above, system controller 12 is programmed to enable automated control of parameters such as concentration, flow rates, temperature, pressure, and residence time required to produce the various desired chemical products. Because automated reactant supply 16a and 16b can provide as much reactant as desired (within the limits of the volume retained of reactants contained therein), it is anticipated that sequential reaction system 10 will be operated continuously, with a minimum of operator supervision, for a period of hours or even days. As shown in FIG. 2, system controller 12 includes a processor 40, a reaction database (memory) 42, and a user interface 44. Preferably, reaction database (memory) 42 includes detailed information relating to a plurality of different chemical products that can be produced by the sequential reaction system of the present invention. The detailed information preferably identifies various chemical products that can be produced, the required starting reactants, the relative volumes of the reactants required to produce a desired volume of each such product, specified process condition parameters, such as temperature, pressure, and flow rates for the reactants, and an identification of the types of reaction modules and an indication of the residence time chambers required to produce each product. The detailed information stored in the associated memory also preferably includes machine language instructions for execution by processor 40 that enable automatic control of the system according to the stored parameters specific to each included reaction and facilitate interaction with an operator via user interface 44, including enabling the operator to make initial decisions for setting up the system controller to run unattended. Preferably, user interface 44 includes a graphic display designed such that a user can select options from a menu. From the displayed menu, the user can select desired chemical products and be provided with details regarding specific types of reaction modules and any additional modules required (such as residence time chambers). Once provided with this information, the user can ensure that the sequential reaction system is properly configured to produce the desired products. The user would ensure that all reactant and solvent supplies and fluid connections within the system are provided and then would activate a start command on using user interface 44, causing processor 40 to control the reactions based on the process control parameters stored within reaction database (memory) 42 for the reactions selected by the user. The reaction database (but not the memory) can be omitted if the user manually enters the reaction parameters on user interface 44.

Figure 3:
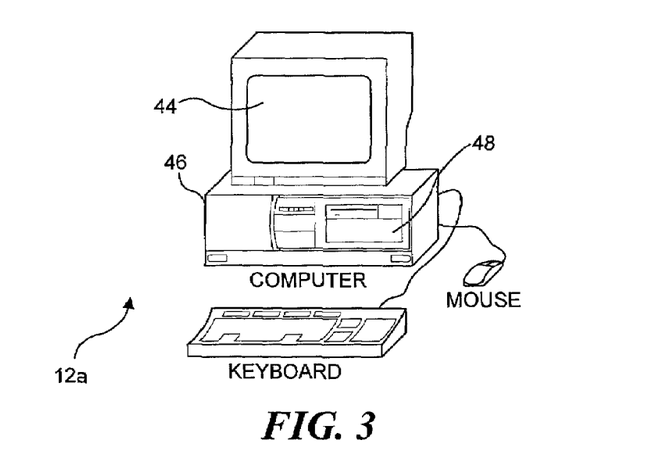
FIG. 3 is a simplified schematic diagram showing a personal computer used as a system controller.

FIG. 3 illustrates a preferred embodiment for a system controller 12a that comprises a personal computer (PC) 46. PC 46 includes processor (not shown), a hard drive 48 on which the reaction database is stored, and user interface display 44. When PC 46 is employed as the system controller, the PC is coupled to the various components of the system through a cable connected to a data port on the PC, such as its serial port, parallel port, or universal serial bus port (none of which are shown in the Figure).

Figure 4:
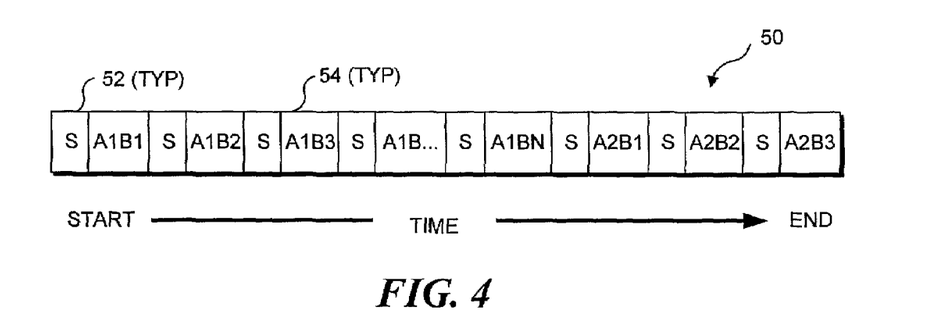
FIG. 4 is a simplified schematic diagram showing of a substance library being sequentially created over a period of time by the sequential reaction system of FIG. 1.

Depending on the algorithm employed by system controller 12, the sequence of desired chemical products generated in response to injecting different combinations of selected reactants into reaction module 22 can be provided in any order desired. FIG. 4 illustrates one possible sequential product output 50. Under this scheme, system controller 12 first causes the supply valve to provide solvent to flush the system, as indicated by the "S" in a solvent block 52. Next, the system controller selects (according to preprogrammed instructions) a combination of reactants A1 and B1 and causes the selected reactants to be introduced into reaction module 22 in the proper proportions and volumes. System controller 12 will control the operation of pumps 24 and heat exchanger 26 to ensure that the proper flow rate of the selected reactants and temperature parameters are established in the reaction module. When the desired chemical product begins to exit the reaction module, automatic online detection device 34 verifies that product rather than solvent is now exiting the reaction module, and the detection device sends a signal indicative of that information to the system controller. System controller 12 then manipulates the outlet valve to direct the detected desired chemical product A1B1 (as indicated by the first of reactant blocks 54) to the appropriate fluid collection chamber 36 in automated product collector 38. As illustrated, the first reaction product is A1B1. Once all of this desired chemical product has been collected, another solvent rinse of the system is carried out, to ensure that no cross reactions occur during the next reaction, and then reactants A1 and B2 are selected and injected into reaction module 22, until the desired volume of the product A1B2 is generated. The system is then once again flushed with solvent, and the next combination of reactants is provided. While in this exemplary illustration, the products are generated according to a logical progression sequence (A1B1, A132, A1B3, etc.), it should be understood that system controller 12 can be programmed to sequentially produce products according to any programmed sequence (for example, A1B1, A3B2, A1B3, etc.). Sequential product output 50 illustrated in FIG. 4 illustrates how the same reaction module is employed to produce a plurality of different desired chemical products in a predetermined sequence, to produce a substance library.

Figure 5:
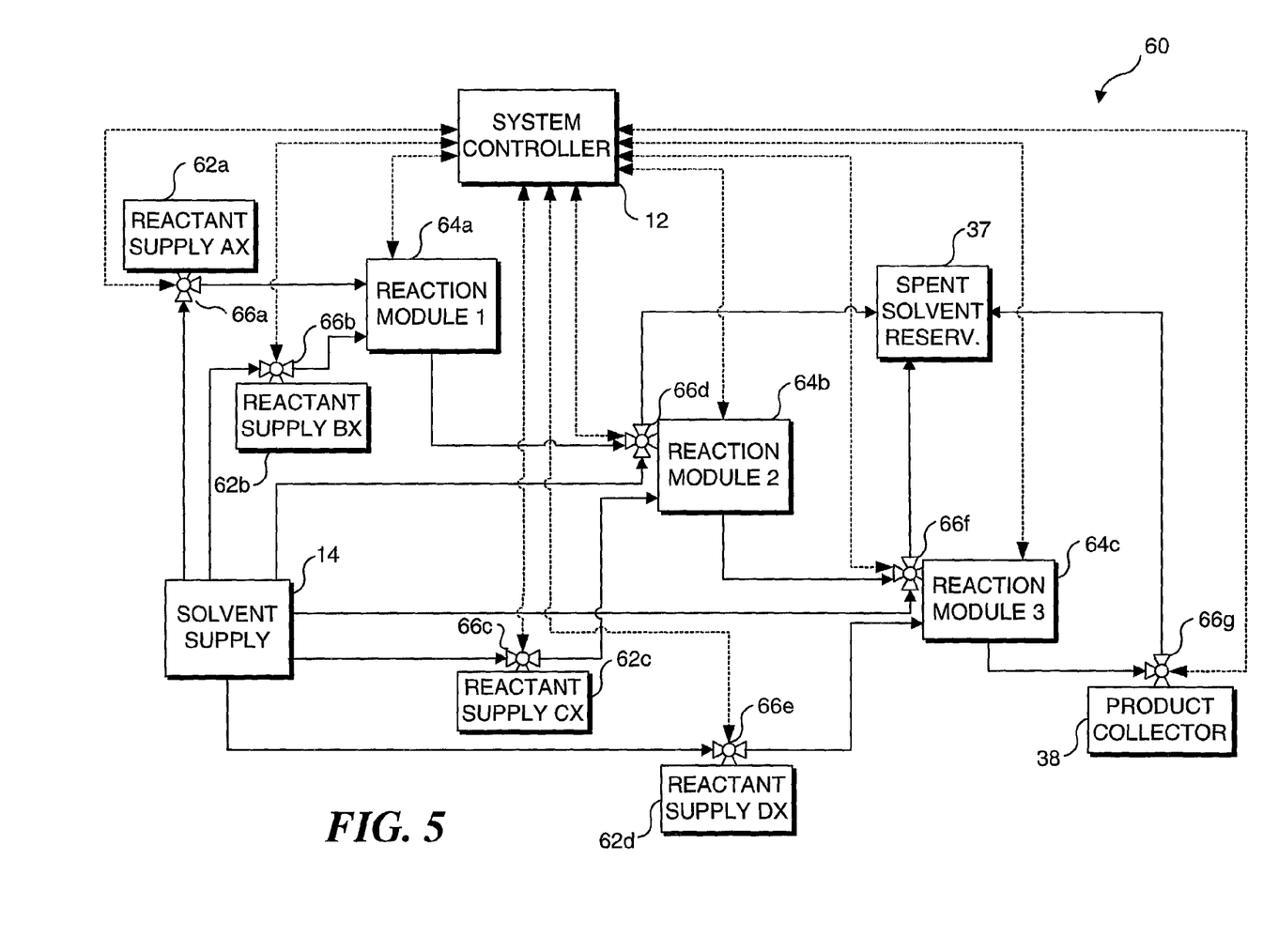
FIG. 5 is a simplified block diagram showing how a plurality of reaction systems can be used in series to produce a product whose production requires a series of sequential reactions to take place.

FIG. 5 illustrates a different sequential production system, in which a plurality of different chemical reactors are combined, such that an intermediate product exiting a first chemical reactor is then combined with a new selected reactant for reaction in a second chemical reactor, etc. These sequential reactions can be carried out until a final desired chemical product is produced. It should be noted that there are numerous types of chemicals which must be produced using a series of sequential reactions, each reaction producing a different intermediate product, until a last reaction generates the final desired chemical product. Peptides, which are built up of different amino acids in a particular sequence, are examples of products that are produced through a series of sequential reactions. However, it should be noted that prior art apparatus and methods for producing peptides using sequential reactions have typically required the use of a solid support (such as inert polymer resin beads) to which the starting reactants must be bonded, and from which the product must be removed. The sequential reaction system of the present invention is adapted to be used to facilitate gas/gas, gas/liquid, and/or liquid/liquid reactions that do not require binding a starting reactant to a support resin, or removing the product from a support resin. Thus, the system of the present invention can be applied to produce a greater variety of different products.

A sequential reaction system 60 illustrated in FIG. 5 includes system controller 12, which is controllably connected to a plurality of different chemical reactors 64a, 64b, and 64c, automated reactant supplies 62a, 62b, 62c, and 62d, and supply valves 66a, 66b, 66c, 66d, 66e, 66f, and 66g. System controller 12 is also controllably connected to automated product collector 38. Sequential reaction system 60 also includes solvent supply 14 and spent solvent reservoir 37. Supply valves 66a-66g preferably each include an integral prime mover capable of actuating the supply valve upon receiving a command from system controller 12, so that the supply valve selectively places a selected reactant (or intermediate product) in fluid communication with the input to one of the chemical reactors to which the output of the supply valve is coupled.

In sequential system 60, first reactant supply 62a and second reactant supply 62b are placed in fluid communication with a first reactor module 64a, via respective supply valves 66a and 66b. Note that supply valves 66a and 66b are selectively placed in fluid communication with solvent supply 14, and that the supply valves are disposed immediately adjacent to their respective reactant supplies. As discussed above, it is preferable for the valves to be disposed immediately adjacent to the reactant supplies, or to be fabricated as integral components of the reactant supplies, to minimize any volume that cannot be flushed with a solvent.

An outlet of first reaction module 64a is in fluid communication with an inlet of a second reaction module 64b, via supply valve 66d. Note that supply valve 66d is also selectively placed in fluid communication with solvent supply 14 and spent solvent reservoir 37. This configuration enables solvent used to flush supply valves 66a and 66b, and first reaction module 64a to be diverted to spent solvent reservoir 37, as well as enabling clean solvent to be directed into supply valve 66d and second reaction module 64b without requiring the solvent to pass through the first reaction module. Thus, the first and second reaction modules can be flushed independently of each other. Reactant supply 62c is also selectively placed in fluid communication with the inlet side of second reaction module 64b, as well as being in fluid communication with solvent supply 14. The discussion of the positioning and flushing of supply valves 66a and 66b also applies to supply valve 66c.

An outlet of second reaction module 64b is selectively placed in fluid communication with an inlet of third reaction module 64c via supply valve 66f, which is also in fluid communication with solvent supply 14 and spent solvent reservoir 37. Supply valve 66f can be used to divert solvent used to flush second reaction module 64a to spent solvent reservoir 37, and to introduce clean solvent into third reaction module 64c for flushing. Reactant supply 62d is also selectively placed in fluid communication with the inlet side of third reaction module 64c, as well as being in fluid communication with solvent supply 14, via supply valve 66e. Supply valve 66e is preferably disposed immediately adjacent to reactant supply 62d for the reasons discussed above. An outlet of reaction module 64c is selectively in fluid communication with both automated product collector 38 and spent solvent reservoir 37 via an outlet valve 66g.

As illustrated, no online detection devices are incorporated into sequential reaction system 60. Thus, system controller 12 actuates supply valves 66a-66g according to a programmed sequence based on the volume of the system and the programmed flow rates. As discussed above, flow rate sensors can be incorporated to provide feedback to system controller 12 as to any differences in actual verses programmed flow rates. It should be understood that the online or offline detection devices discussed above can optionally be included in sequential reaction system 60, if desired. It should also be understood that if more than three sequential reactions are required to produce the desired product, then additional reaction modules and reactant supplies can be added, with the corresponding supply valves. It should also be understood that the chemical reaction modules preferably include pumps and heat exchangers (and residence time chambers, as required) as described above.

To use sequential reaction system 60, one reactant from first reactant supply 62a and one reactant from second reactant supply 62b (if required) are injected into first reaction module 64a. Preferably, before any use, the entire system is first flushed with solvent. The first intermediate product exits reaction module 64a and is then selectively injected, along with a reactant from reactant supply 62c, into second reaction module 64b. A second intermediate product from reaction module 64b is then injected, along with an automatically selected reactant from reactant supply 62d, into third reaction module 64c. The final desired chemical product is then collected by automated product collector 38.

Note that once first reaction module 64a completes the production of the first intermediate product, a different combination of reactants from first reactant supply 62a, and second reactant supply 62b can be injected into first reaction module 64a. Supply valves 66a and 66b are actuated to selectively provide fluid communication with solvent supply 14, to causing first reaction module 64a to be flushed with solvent. Supply valve 66d is actuated by system controller 12 after the solvent flush exits the first reaction module, so that the spent solvent is directed into spent solvent reservoir 37, rather than into the second reaction module. Then, the system controller actuates supply valves 66a and 66b, and reactant supplies 62a and 62b, to provide the selected reactants required for the next programmed reaction, causing the first reaction module to begin to produce a different intermediate product required to produce a different final desired chemical product. Thus, sequential reaction system 60 can be maintained in continuous operation, even when different reaction modules are processing different reactants and intermediate products relating to different final desired chemical products.

While sequential reaction system 60 has been described as preferably incorporating reaction modules that generate intermediate or final desired chemical products generally by reacting two reactants (or a reactant and an intermediate product), it should be understood that reaction modules adapted to facilitate reactions utilizing more than two reactants can also be used. Furthermore, some reactions, such as those involving passing one reactant over a catalyst impregnated surface, or a photochemical reaction that is initiated by applying light of the appropriate wavelength to a single reactant, can produce a desired or intermediate product from a single reactant. Thus, reaction modules adapted to generate intermediate products or a desired final product from a single reactant or intermediate product can also be employed. The above-described configuration in which two automated reactant supplies, or one intermediate product and once automated reactant supply are reacted in successive chemical reaction modules is merely exemplary, and should not be considered as limiting the scope of the present invention.

Figure 6:
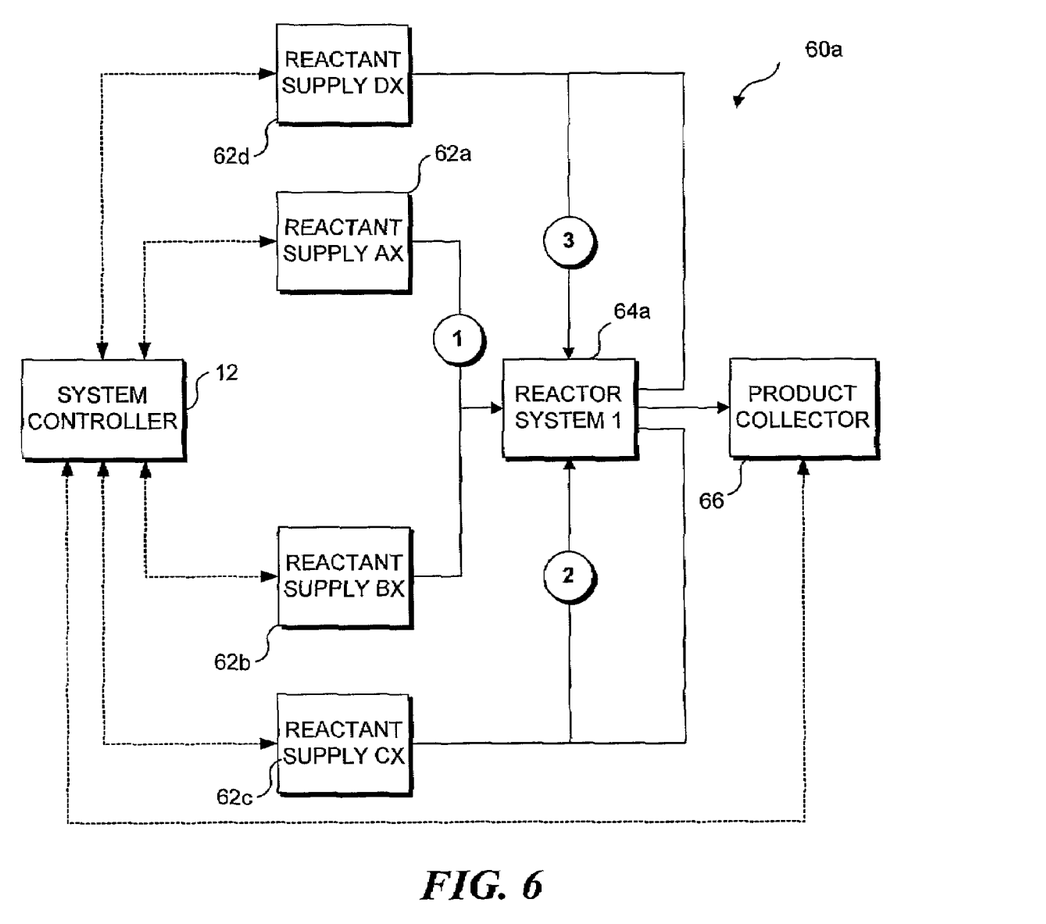
FIG. 6 is a simplified block diagram showing how a single reaction system can be used to produce a product whose production requires a series of sequential reactions to take place.

FIG. 6 illustrates a sequential reaction system 60a, in which a product requiring three sequential reactions is generated using only a single reaction module, as opposed to the three reaction modules illustrated in FIG. 5. Prior to injecting any reactants, sequential reaction system 60a is flushed with a solvent as described above in conjunction with FIG. 1. Then, a desired volume of reactants selected from a first reactant supply 62a, and a second reactant supply 62b are injected into reaction module 64a. The first injection into reaction module 64a is indicated by a numeral 1 in a circle illustrated on the fluid path connecting first reactant supply 62a and second reactant supply 62b to reaction module 64a. The first intermediate product exiting reaction module 64a is then combined with a reactant selected by the system controller from a reactant supply 62c (or alternatively, from either of reactant supplies 62a or 62b), and once again injected into reaction module 64a, rather than into a different reaction module. This second injection into reaction module 64a is indicated by a numeral 2 in a circle that is disposed on the fluid path connecting third reactant supply 62c and a product outlet of reaction module 64a, to the inlet of reaction module 64a. Note that system controller 12 must both halt the flow of reactants from first reactant supply 62a and a second reactant supply 62b once the desired volume of each reactant has been delivered, and flush the system with solvent, before injecting the intermediate product exiting from reaction module 64a and a reactant from third reactant supply 62c into reaction module 64a. Once all of the intermediate product of the second sequential reaction exits reaction module 64a, the system is again flushed with solvent and that intermediate product is injected with yet another reactant selected from reactant supply 62d (or from any of the other reactant supplies) into reaction module 64a. This third injection into reaction module 64a is indicated by a numeral 3 in a circle that is disposed on the fluid path connecting fourth reactant supply 62d, and a product outlet of reaction module 64a to the inlet of reaction module 64a. The final desired chemical product is then collected by automated product collector 66.

It should be understood that reaction module 64a normally includes only a single product outlet, and that the three distinct product outlets illustrated in FIG. 6 are meant to represent the single product outlet being used sequentially in three different successive time periods to convey two intermediate products and the final desired chemical product. It should also be understood that the supply valves, solvent supply and spent solvent reservoir discussed in detail with respect to FIGS. 1 and 5 are also included in sequential reaction system 60a, although not shown. Note that while sequential reaction system 60a can complete the same three step (or more) sequential reactions as sequential reaction system 60, but using only a single reaction module, the throughput of sequential reaction system 60a is less than the throughput of sequential reaction system 60, because reactants from first reactant supply 62a and second reactant supply 62b must be cycled on and off, so that reaction module 64a can process other reactants. In contrast, reaction module 64a of sequential reaction system 60 can be operated continuously to combine reactants from first reactant supply 62a and second reactant supply 62b. In circumstances where the volume of product produced is less important than minimizing equipment costs, single reactor sequential reaction system 60a is preferred.

Again, it should be understood that while the above description is directed to an example in which a final desired chemical product is produced from two reactants/intermediate products, a similar sequential system can be utilized in conjunction with reactions employing a single reactant/intermediate product, or more than two reactants/intermediate products.

Sequentially Generating a Substance Library: "Product Package Running" Synthesis The following steps are automatically controlled with the present invention. After the operator starts the software program that controls the process, the following steps are executed automatically (refer to FIG. 1):

Step 1: Initialization of sequential reaction system begins by pumping heat transfer medium of the desired temperature from heat exchanger 26 (and optional heat exchanger 30, if included) through reaction module 22 (and optional residence time chamber 32, if included).

Step 2: Flush the entire system using solvent from solvent supply 14, until solvent exits reaction module 22. The solvent flush may be executed using an accelerated flow rate to reduce the time required for flushing.

Step 3: Allow the system to achieve thermal equilibrium, as indicated by a difference of no more than 2° K. between the temperature of the heat transfer medium and the temperature of chemical reactor 28 according to temperature sensors 25 disposed on or in the chemical reactor 28 (and residence time chamber 32, if included).

Step 4: Select a reactant from automated reactant supply 16a and a reactant from automated reactant supply 16b for injection into reaction module 22, enabling the generation of a desired chemical product.

Step 5: The desired chemical product exits reaction module 22, reaching online detection device 34, which verifies that the material is a desired chemical product rather than solvent. The desired chemical product is directed to an appropriate fluid chamber 36 in automated product collector 38 (or to spent solvent reservoir 37, if the material is the spent solvent rather than a desired chemical product).

Step 6: A cleaning/rinsing cycle is performed by flushing the system with solvent.

Step 7: While the selected reactant from automated reactant supply 16a is maintained, selection of a different reactant from automated reactant supply 16b is carried out, enabling the synthesis of a different product. Alternatively, the reactant selected from automated reactant supply 16b can be maintained while a different reactant is selected from automated reactant supply 16a, or the reactants selected from both such supplies can be changed by system controller 12 actuating the appropriate supply valves 19a and/or 19b.

Step 8: Interrupted by the solvent cleaning/rinsing cycles, system controller 12 selects still further reactants from automated reactant supplies 16a and/or 16b to produce different desired chemical products, until each desired combination of one reactant from one of automated reactant supplies 16a or 16b and a different reactant from the other of automated reactant supply 16b or 16a has been achieved.

Since the flow rate (reaction time) and temperature parameters for each reaction can be adjusted individually, sequential product packages (illustrated in FIG. 4) whose products require different reaction conditions can readily be produced.

Description of an Exemplary Substance Library—Sequential Production of Amides from Amines Using sequential reaction system 10, a combination of liquid acetic anhydride (selected from automated reactant supply 16b as reactant B1) with 24 different amines (selected from automated reactant supply 16a as reactants A1-A24) was carried out. Triethylamine was added to each reaction to capture the acetic acid formed during synthesis. The reaction follows the equation:

The goal was to sequentially produce a substance library of 24 amides in a continuous process. To achieve this result, amine stock solutions (Reactants A1-A24) were distributed by a multi port rotary valve to a piston pump from where they were fed at a desired controlled flow rate into a microreactor. The acetic anhydride solution (Reactant B) was delivered into the second inlet of the microreactor by another pump. Both pump inlets could selectively be switched to a solvent supply to provide solvent to rinse the system after each reaction. Note that a larger substance library can be created either by increasing the number of different amines used for Reactant A, or by using more than one Reactant B.

Stock Solutions

A: 0.088 mole of amine+10.84 g (0.11 mole) triethylamine+dioxane or DMF to give 70 ml of a 1.26 M solution.

B: 22.05 g (0.22 mole) of acetic anhydride+180 ml dioxane or DMF to give 200 ml of a 1.08 M Solution In a series of experiments, different conditions such as temperature and flow rate (residence time) were employed. For example a typical experiment was carried out as follows:

The heat exchanger was set to provide a 80° C. temperature conditioned fluid media, and the flow rate for each selected reactant was adjusted to 0.7 ml/min (yielding a residence time in the reaction system of about 1 minute). Reactant A1 and B1 were pumped through the system for 10 minutes. During this time, the internal temperature of the chemical reactor was monitored. Depending upon the reaction, a temperature of 56-62° C. was measured in the reaction module. After about 5 minutes, the desired chemical product began to flow into the collector and was collected for 5 minutes, yielding 7 ml of the product. Then, the system was flushed for 2 minutes, with a higher flow of solvent (6.5 ml/min). After this flushing step, reactant A2 was introduced for about 10 minutes. The process was then repeated for different time and temperature conditions.

RESULTS/ANALYSIS

A typical product yield of 80-95% was obtained, as determined by gas chromatography. The procedure and system employed enabled the synthesis of 4 to 68 g of amides per hour, depending on the molecular weight of the desired amide product produced. The time for the generation of one analytical sample was about 10 minutes. Reaction conditions and parameters for each of the 24 sequential reaction are set forth in Table 1, below.

TABLE 1

| No. | Amine | Reaction time/mm | Yield [%] | Throughput [g/h] |
|---|---|---|---|---|
| Unbranched aliphatic amine | | | | |
| 1 | 1-propylamine | 13 | 98 | 6 |
| 2 | 1-butylamine | 13 | 99 | 7 |
| 3 | 1-pentylamine | 2 | 99 | 50 |
| 4 | 1-hexlyamine | 4 | 99 | 28 |
| 5 | 1-heptylamine | 1 | 94 | 7 |
| 6 | 1-octylamine | 4 | 99 | 33 |
| 7 | 1-nonylamine | 2 | 95 | 68 |
| Branched ahphatic amines | | | | |
| 8 | 3-methyl-2-butylamine | 1 | 85 | 5 |
| 9 | 2-methyl-2-butylamine | 1 | 75 | 4 |
| 10 | t-butylamine | 13 | 70 | 5 |
| Cyclic amines | | | | |
| 11 | cyclopentylamine | 2 | 99 | 50 |
| 12 | cyclohexylamine | 13 | 89 | 8 |
| 13 | cycloheptylamine | 2 | 83 | 50 |
| Aromatic amines | | | | |
| 14 | Aniline | 1 | 99 | 6 |
| 15 | 1-naphthylamine | 1 | 46 | 4 |

CONCLUSION

A major advantage of automated sequential synthesis of chemical products as provided by the present invention is the capability to individually adjust both the reaction time and temperature for each different reaction within a sequence. Such flexibility enables system temperature and flow rate to be tailored to each reaction. Of the 24 amines used as reactants in the above exemplary sequence, several are quite reactive, and some are much less reactive. For amines that are highly reactive, high flow rates and low temperatures are appropriate. For less reactive amines, high temperatures and lower flow rates are required. Note that each desired chemical product can be produced in a desired amount, regardless of the amounts of the other desired chemical products produced in a sequence. Finally, because the system of the present invention is automated, a substance library can be created with minimal operator involvement, once the system controller is programmed and the system is supplied with the required reagents.

Exemplary chemical Reaction Performed in a Stacked Simple Plate Reactor

The described chemical reaction belongs to the class of organometallic conversions, i.e., the addition of an organolithium compound to a carbonyl compound. cyclohexanone (1) reacts in a one step procedure with methyl lithium to produce the 1,2-addition product 1-methyl-cyclohexanol (2).

Supply of the Starting Materials:

1. a 1.5 molar solution of methyl lithium dissolved in diethylether (commercially available in 100-ml bottles sealed with a septum).

2. Preparation of 100 ml of a solution of 13.2 grams (0.15 moles) of cyclohexanone (commercially available liquid) in dry diethylether.

Solution No. 2 is transferred into a pressure compensated bottle with tube connectors. Both solutions are connected to an argon atmosphere prior to use to avoid hydrolysation with air.

Thermal Conditioning and Setting up of the system:

The reactor temperature is adjusted to −20° C. by cryostats, which are connected to the heat exchangers of the reactor. Solvent (diethylether) is pumped continuously through the complete system until the solvent flow leaving the reactor has reached −20° C.

Performing the Reaction

After reaching thermal equilibrium, the two-reactant solutions are transferred by individual pumps via Teflon™ tubing into the reactor. The pump rate is set to 1 ml/min for each reactant. The two reactant flows are each divided into four parallel laminar flow streams with dimensions of several micrometers. They enter the inter-digital-mixer located under heat exchanger 1, which is a cross flow type heat exchanger, where they are cooled to the appropriate temperature (−20° C.). It should be noted that this temperature is a function of the desired reaction. In some cases, each reactant may require pre-treatment to obtain a different reactant temperature. Thus, the stacked simple plate reactor may preferably include a heat exchanger for modifying the temperature of each reactant. Of course, if the reactant temperatures are to be the same, then a stacked simple plate reactor can be designed with a single heat exchanger to pretreat both reactants.

In the inter-digital-mixer, the two reactant flows are each divided again into 12 individual laminar flow streams for each reactant. These 24 streams enter the four lamination channels in groups of six streams, where each group of six streams are combined again (stacked onto each other). From here, the four groups of six stacked fluid streams enter the four mixing chambers (which are placed under heat exchanger 2), and the four groups of six stacked fluid streams are reduced in thickness so that diffusion mixing will occur. Thus, in each of the four groups of six stacked fluid streams, three single streams of reactant A are united with three single streams of reactant B. After mixing, the reactants exit the four mixing chambers at two exits per mixing chamber, thus resulting in eight mixed reactant streams. These eight mixed reactant streams enter the eight reaction channels, which are sandwiched between heat exchangers 3 and 4. It is within the reaction channels that the final reaction takes place, and it is here that the most heat is generally produced; thus the reaction channels are sandwiched between two heat exchangers.

Heat transfer is extremely efficient due to the high surface to volume ratio, to the selection of an extremely thermally transparent material for the simple plates that form the heat exchanger (by the control of the material and/or the thickness of the simple plates), and to the thinness of the simple plates (the distance between the mixing zone and heat exchanger is in the range of a few micrometers). Thus, the heat of the exothermic reaction can be reduced to 1-2° K. above the determined reaction temperature.

The internal volume of the mixing zone is approximately 1 ml, providing a residence time of 30 seconds, during which the majority of the reaction is completed. For reactions that need a longer reaction time, an additional residence time chamber can be added to the reactor, either by using additional simple plates, or by adding a separate residence chamber module downstream of the reactor.

The resultant product stream leaves the reactor via a Teflon™ tube into a collection flask that is filled with 2N hydrochloric acid. Instant quenching of the addition adduct and excess reagent takes place.

Benefits of the Simple Plate Stacked Reactor:

Advantages of the stacked simple plate reactor system are precise temperature control, exact adjustment of reaction time, and eliminating the need of a protective atmosphere, since the reactor is a closed environment. Enhanced safety is provided due to the small quantities of material, and the closed environment operating conditions.

The system is especially advantageous when large quantities of product are required, because the reactor can work continuously, and can be operated for hours, even up to days, without maintenance. Accordingly, automated production of large amounts of the desired product without the loss of efficiency and safety can be achieved. Additional product can be obtained by operating additional reactors in parallel under identical operating conditions.

System Description:

The reactants are provided in conventional laboratory bottles with tube connectors. The bottles are connected to a pump module by Teflon™ tubes. Inside a pump module disposed upstream from the pumps are three way valves, which are connected to the reactants, the solvents, and the pump inlet. For conditioning the stacked simple plate reactor, the valves are set to the solvents, so that the pumps first fill the whole system with solvent until the stacked simple plate reactor reaches thermal equilibrium. Then the valves are set to the reactants, enabling the pumps to deliver the reactants into the stacked simple plate reactor. A filter is placed inline between the pump outlet and reactor inlet to avoid clogging of the system by particulates. Fluidic connection of pumps and reactor can be achieved by commercially available HPLC fittings. Controlling the temperature of the stacked simple plate reactor is achieved by pumping heat transfer media from a cryostat into the internal heat exchangers of the stacked simple plate reactor. Product coming out of the system is collected in a conventional laboratory bottle.

Measuring and Automation Control Devices:

All pumps, valves, and cryostats are preferably controlled by a microcontroller or computer, programmed with appropriate software, enabling convenient adjustment and control of the system. The following sensor devices are optionally used to provide analog signals that are converted to digital signals for input to the microcontroller or computer, to facilitate more efficient manual or automated control of the chemical process:

Pressure sensors disposed downstream from each pump and at the inlet and outlets of the stacked simple plate reactor.

Temperature sensors integrated in the stacked simple plate reactor and disposed close to the mixing zone and at the reactor outlet.

Optional flow sensors introduced into each reactant stream for improved flow adjustment.

Excellent control and adjustment of flow and ratio of the reactants, determination of the pressure buildup inside the system by differential pressure measurement, and exact adjustment and control of the reaction temperature can thus be achieved.

Although the present invention has been described in connection with the preferred form of practicing it and modifications thereto, those of ordinary skill in the art will understand that many further modifications can be made to the present invention within the scope of the claims that follow. Accordingly, it is not intended that the scope of the invention in any way be limited by the above description, but instead be determined entirely by reference to the claims that follow.

The invention claimed is:

1. An automated sequential reaction system for automatically and sequentially producing a substance library of different desired chemical products from a plurality of reactants in accord with a programmed series of steps, comprising:
   (a) a first automated reactant supply comprising a plurality of separate reactant chambers, each adapted to be filled with a different reactant;
   (b) a first supply valve that is automatically actuatable and is connected to the first automated reactant supply to select a desired first reactant from among the plurality of separate reactant chambers;
   (c) a solvent supply, said solvent supply being configured to contain a solvent for flushing said automated sequential reaction system;
   (d) a reaction module coupled in fluid communication with said first supply valve, such that a reactant chamber selected from within said automated first reactant supply by the first supply valve is placed in fluid communication with said reaction module, said reaction module including a general purpose chemical reactor that is operable to produce the substance library of different desired chemical products from the plurality of reactants;
   (e) an output valve that is automatically actuatable and is coupled in fluid communication with the reaction module to receive a desired chemical product, said desired chemical product contributing to the substance library of different desired chemical products;
   (f) an automated product collector in fluid communication with said output valve to receive the desired chemical product and comprising a plurality of product chambers, each product chamber being adapted to be filled with a different desired product to produce the substance library of different desired chemical products; and
   (g) a system controller controllably connected to the first automated reactant supply, the first supply valve, and the automated product collector, said system controller being programmed to monitor and control production of the plurality of desired chemical products by the automated sequential reaction system, the system controller being configured to operate the automated sequential reactant system as required to produce the substance library of different desired chemical products, the system controller implementing the steps of:
      (i) controlling the first automated reactant supply and the first supply valve to introduce each reactant required to produce the substance library of different desired chemical products in a desired order; and
      (ii) controlling the solvent supply to flush the general purpose reactor with the solvent as required, such that while the automated sequential reaction system is operational a fluid discharged from the reaction module alternates between:
         (A) one of the different desired chemical products; and
         (B) the solvent and any residual chemical product that is flushed from the reactor by the solvent.

2. The automated sequential reaction system of claim 1, wherein said solvent supply is selectively placed into fluid communication with the reaction module by the first supply valve under control of the system controller, to enable a solvent to flow from said solvent supply into said reaction module.

3. The automated sequential reaction system of claim 2, wherein said automated product collector further comprises a spent solvent reservoir, said spent solvent reservoir being adapted to contain a spent solvent that has been used to flush said sequential reaction system, said spent solvent reservoir being selectively placed into fluid communication with the reaction module by the output valve under control of said system controller, to enable a spent solvent to flow from the reaction module into said spent solvent reservoir.

4. The automated sequential reaction system of claim 1, wherein the solvent supply is part of the first automated reactant supply.

5. The automated sequential reaction system of claim 1, further comprising an automated detector disposed between the output valve and the reaction module and coupled to the system controller, said automated detector providing an output signal to the system controller that is indicative of whether a spent solvent or a desired chemical product is flowing from the reaction module, said system controller responding to the output signal to actuate the output valve to:
   (a) selectively couple the reaction module in fluid communication with the automated product collector if the output signal indicates that a desired product is flowing from the reaction module; and
   (b) selectively couple the reaction module in fluid communication with the spent solvent reservoir if the output signal indicates that a spent solvent is flowing from the reaction module.

6. The automated sequential reaction system of claim 1, further comprising a heat exchanger controllably connected to said system controller, said heat exchanger being configured to enable the system controller to control a temperature within said reaction module.

7. The automated sequential reaction system of claim 6, wherein said heat exchanger is disposed within said reaction module.

8. The automated sequential reaction system of claim 1, further comprising a pump having an inlet in fluid communication with said supply valve, and an outlet coupled in fluid communication with an inlet to the chemical reactor, said pump being controllably connected to said system controller to enable control of a flow rate of a first desired reactant into the chemical reactor.

9. The automated sequential reaction system of claim 1, wherein the reaction module includes a residence time chamber in fluid communication with an outlet of the chemical reactor, said residence time chamber providing additional time for a desired chemical product to be produced and having an outlet coupled in fluid communication with the output valve.

10. The automated sequential reaction system of claim 1, wherein said chemical reactor comprises a microreactor.

11. The automated sequential reaction system of claim 1, wherein said system controller includes a memory, a processor, and a user interface, said memory storing machine instructions that define the automated sequence of steps and which are executed by the processor to effect automatic control of the automated sequential reaction system.

12. The automated sequential reaction system of claim 8, wherein said outlet valve comprises a proportional valve configured to act as a throttle to enable a pressure along a reaction path to be selectively varied.

13. The automated sequential reaction system of claim 1, further comprising a second supply valve, and a second automated reactant supply, said second automated reactant supply comprising a plurality of separate reactant chambers, each adapted to be filled with a different reactant, said second supply valve being automatically actuatable and connected to the second automated reactant supply to select a second desired reactant from among the plurality of separate reactant chambers included therein under control of said system controller, said first desired reactant and said second desired reactant being supplied to the reaction module to produce the desired product.

14. An automated sequential reaction system for sequentially producing a substance library of a plurality of different chemical products using selected desired reactants from among a plurality of different reactants, comprising:
  (a) a first automated fluid supply comprising a plurality of first separately addressable volumes that are selectively coupled in fluid communication with a first outlet, each volume being adapted to contain a different reactant;
  (b) a second automated fluid supply comprising a plurality of second separately addressable volumes that are selectively coupled in fluid communication with a second outlet, each volume being adapted to contain a different reactant;
  (c) a chemical reactor in fluid communication with said first outlet to receive a first desired reactant therefrom and with said second outlet to receive a second desired reactant therefrom, said chemical reactor being generally configured for sequentially producing the plurality of different chemical products by reacting successive different first and second desired reactants;
  (d) a solvent supply adapted to contain a solvent and selectively provide the solvent to the chemical reactor for flushing the chemical reactor after each of the plurality of different chemical products has been produced thereby;
  (e) an automated fluid collector comprising a plurality of separate fluid volumes, each fluid volume being selectively coupled to the chemical reactor to receive a different chemical product therefrom;
  (f) a spent solvent reservoir that is selectively coupled in fluid communication with the chemical reactor, to receive a spent solvent that was used for flushing the chemical reactor after each different desired chemical product has been produced thereby; and
  (g) a system controller controllably connected to the first automated fluid supply, the second automated fluid supply, the solvent supply, the chemical reactor, the spent solvent reservoir, and the automated fluid collector, said system controller being programmed to operate the automated sequential reactant system as required to produce the substance library of different desired chemical products, the system controller implementing the steps of:
    (i) controlling the first automated reactant supply, the first supply valve, the second automated reactant supply, and the second supply valve to introduce each reactant required to produce the substance library of different desired chemical products in a desired order; and
    (ii) controlling the solvent supply to flush the chemical reactor with the solvent as required, such that while the automated sequential reaction system is operational, a fluid discharged from the reaction module comprises either one of the different desired chemical products or the solvent along with any residual chemical product that is flushed from the reactor by the solvent.

15. The automated sequential reaction system of claim 14, further comprising a pump in fluid communication with said first outlet of said first fluid supply, with said second outlet of said second fluid supply, and with said chemical reactor, said pump being controllably connected to said system controller, which controls a flow rate of the first and second desired reactants through said automated sequential reaction system with the pump.

16. The automated sequential reaction system of claim 14, further comprising a residence time chamber in fluid communication with an outlet of said chemical reactor, said residence time chamber providing additional time for a chemical product to be produced and having an outlet coupled in fluid communication with the automated fluid collector and the spent solvent reservoir.

17. The automated sequential reaction system of claim 14, further comprising a detector in fluid communication with an outlet of said reactor, said detector producing a signal indicative of the type of fluid being discharged, said detector being controllably connected to said system controller, said system controller directing a spent solvent to said spent solvent reservoir and a desired chemical product to said automated fluid collector.

18. The automated sequential reaction system of claim 14, further comprising a heat exchanger controllably connected to said system controller, said heat exchanger being configured to enable the system controller to control a temperature within said chemical reactor.

19. An automated sequential reaction system for automatically and sequentially producing a substance library of different desired chemical products from a plurality of reactants in accord with a programmed series of steps, comprising:
  (a) a first automated reactant supply comprising a plurality of separate reactant chambers, each adapted to be filled with a different reactant;
  (b) a first supply valve that is automatically actuatable and is connected to the first automated reactant supply to select a first desired reactant from among the plurality of separate reactant chambers;
  (c) a reaction module coupled in fluid communication with said first supply valve, such that a reactant chamber selected from within said automated reactant supply by the first supply valve is placed in fluid communication with said reaction module, said reaction module including a general purpose chemical reactor that is operable to produce the substance library of different desired chemical products from the plurality of reactants;
  (d) an output valve that is automatically actuatable and is coupled in fluid communication with the reaction module to receive a desired chemical product, said desired chemical product contributing to the substance library of different desired chemical products;
  (e) an automated product collector in fluid communication with said output valve to receive the desired chemical product and comprising a plurality of product chambers, each product chamber being adapted to be filled with a different desired product to produce the substance library of different desired chemical products;
  (f) a system controller controllably connected to the first automated reactant supply, the first supply valve, the reaction module, and the automated product collector, said system controller being programmed to monitor and control production of the plurality of desired chemical products by the automated sequential reaction system, including controlling the first supply valve to select the first desired reactant, and controlling the output valve to select a product chamber into which the desired product is directed; and
  (g) an automated detector disposed between the output valve and the reaction module and coupled to the system controller, said automated detector providing an output signal to the system controller that is indicative of whether a spent solvent or a desired chemical product is flowing from the reaction module, said system controller responding to the output signal to actuate the output valve to:
  (i) selectively couple the reaction module in fluid communication with the automated product collector if the output signal indicates that a desired product is flowing from the reaction module; and
  (ii) selectively couple the reaction module in fluid communication with a spent solvent reservoir if the output signal indicates that a spent solvent is flowing from the reaction module.

20. An automated sequential reaction system for automatically and sequentially producing a substance library of different desired chemical products from a plurality of reactants in accord with a programmed series of steps, comprising:
  (a) a reactor configured to generate a desired chemical product from at least one reactant;
  (b) a first reactant delivery structure configured to selectively deliver one of a plurality of different first reactants to the reactor;
  (c) a solvent delivery structure configured to selectively deliver a solvent to the reactor, to enable the reactor to be flushed with the solvent; and
  (d) a system controller controllably connected to said first reactant delivery structure and said solvent delivery structure, the system controller being configured to operate the automated sequential reactant system as required to produce the substance library of different desired chemical products, the system controller implementing the steps of:
    (i) controlling the first reactant delivery structure to introduce a reactant required to produce a first desired product into the reactor for a period of time sufficient to produce a desired quantity of the first desired product;
    (ii) controlling the solvent delivery structure to flush the reactor with the solvent after the desired quantity of the first desired product has been produced; and
    (iii) repeating steps (i) and (ii) for each additional reactant required to produce an additional desired product, such that a volume of solvent separates each different desired product discharged from the reactor to produce the substance library of different desired chemical products, such that a flow of fluid discharged from the reactor comprises different desired chemical products separated by the solvent.

21. An automated sequential reaction system for automatically and sequentially producing a substance library of different desired chemical products from a plurality of reactants in accord with a programmed series of steps, comprising:
  (a) a reactor configured to generate a desired chemical product from at least one reactant;
  (b) a first reactant delivery structure configured to selectively deliver one of a plurality of different first reactants to the reactor;
  (c) a solvent delivery structure configured to selectively deliver a solvent to the reactor, to enable the reactor to be flushed with the solvent;
  (d) an output valve that is automatically actuatable and is coupled in fluid communication with the reactor to receive a fluid being discharged from the reactor;
  (e) an automated detector disposed between the output valve and the reactor, said automated detector providing an output signal that is indicative of whether the fluid being discharged from the reactor comprises the solvent; and
  (f) a system controller controllably connected to said first reactant delivery structure, said solvent delivery structure, said output valve, and said automated detector, the system controller being configured to operate the automated sequential reactant system as required to produce the substance library of different desired chemical products, the system controller implementing the steps of:
    (i) controlling the first reactant delivery structure to introduce into the reactor each reactant required to produce the substance library of different desired chemical products in a desired order;
    (ii) controlling the solvent delivery structure to flush the reactor with the solvent as required; and
    (iii) controlling the state of the output valve based on the signal provided by the automated detector, such that when the signal from the automated detector indicates that a solvent is being discharged from the reactor module, the output valve is placed in fluid communication with the spent solvent collection volume, and when the signal from the automated detector indicates that a solvent is not being discharged from the reactor, the output valve is placed in fluid communication with the automated product collectors

* * * * *